United States Patent [19]

Mewshaw et al.

[11] Patent Number: 5,250,537
[45] Date of Patent: Oct. 5, 1993

[54] 5,6,7,8,9,10-HEXAHYDRO-7,10-IMINOCYCLOHEPT[B]INDOLE,-6,7,8,9,10-HEXAHYDRO-7,11-IMINO-5H-CYCLOOCT[B]INDOLE AND SUBSTITUTED DERIVATIVES

[75] Inventors: Richard E. Mewshaw, Baltimore; Carl Kaiser, Millersville; Mary E. Abreu, Baltimore, all of Md.

[73] Assignee: Scios Nova Inc., Mountain View, Calif.

[21] Appl. No.: 850,761

[22] Filed: Mar. 13, 1992

[51] Int. Cl.$^5$ .................. A61K 31/435; C07D 471/18; C07D 471/20
[52] U.S. Cl. .................... 514/278; 514/286; 546/16; 546/63; 546/70
[58] Field of Search ............ 546/16, 63, 70; 514/278, 286

[56] References Cited

U.S. PATENT DOCUMENTS 4,174,453 11/1979 Berger .................................. 546/85
4,360,673 11/1982 Berger et al. ......................... 546/70

OTHER PUBLICATIONS

Abou-Gharbia et al. Med. Chem. 30, 1818–1823 (1987).
Axelsson et al. Psychopharmacology 104, 287–292 (1991).
Welch et al. J. Med. Chem. 23, 949–952 (1980).
Harbert et al. J. Med. Chem. 23, 635–643 (1980).
Harbert et al. Mol. Pharm. 17, 38–42 (1980).

Primary Examiner—Mukund J. Shah
Assistant Examiner—P. Datlow
Attorney, Agent, or Firm—Vanessa L. Appleby; Vincent Fabiano; Pete Shearer

[57] ABSTRACT 5,6,7,8,9,10-Hexahydro-7,10-iminocyclohept[b]indole, 6,7,8,9,10,11-hexahydro-7,11-imino-5H-cyclooct[b]indole and substituted derivatives are effective in the treatment of psychoses with limited liability to produce concomitant adverse extrapyramidal symptoms. These compounds are also useful for treating other central nervous system and cardiovascular disorders.

15 Claims, No Drawings

5,6,7,8,9,10-HEXAHYDRO-7,10-IMINOCY-CLOHEPT[B]INDOLE,-6,7,8,9,10-HEXAHYDRO-7,11-IMINO-5H-CYCLOOCT[B]INDOLE AND SUBSTITUTED DERIVATIVES

BACKGROUND OF THE INVENTION

1. Field of the Invention

This invention relates to novel pharmaceutical compositions containing as an active ingredient compounds which produce antipsychotic activity predicted to be essentially free of extrapyramidal symptoms (EPS) and to a method of producing antipsychotic activity expected to be essentially free of EPS which comprises administering non-toxic, effective quantities of these compounds to an animal. EPS are some of the most undesirable and common side effects produced by antipsychotic or neuroleptic drugs. The compounds which are the active ingredients used in the composition and methods of this invention have a profile of binding to serotonin (5-HT$_2$), dopamine (D-2), and sigma receptors suggestive of antipsychotic activity with essentially no liability to produce EPS. By virtue of their 5-HT$_2$ antagonist activity these compounds also are useful in treating other disorders of the cardiovascular and central nervous systems.

2. Description of Related Information

A variety of evidence [I. Creese, D. R. Burt, and S. H. Snyder, Science, 192, 481 (1976); E. F. Domino and B. Kovacic, Mod. Problems Pharmacopsychiat. 21, 21 (1983); A. J. Stoessl, C. T. Dourish, and S. D. Iverson, Psychopharmacol., 98, 372 (1989)] suggests that EPS associated with traditional antipsychotic agents results from the antagonist activity of these drugs at D-2 dopamine receptors. Recent studies have shown that classical antipsychotic drugs including chlorpromazine and haloperidol, bind to both dopamine D-2 and sigma receptors and that their antipsychotic actions may result from blockade at both of these classes of receptors which are associated with production of psychoses [S. H. Snyder and B. L. Largent, J. Neuropsychol. 1, 7 (1988)]. In animals, antipsychotic-like actions without concomitant effects associated with EPS have been observed with sigma ligands that lack significant affinity for dopamine D-2 receptors [W. Guy, G. Manon and W. H. Wilson, Drug Dev. Res. 3, (1983); D. Taylor and J. Dekleva, Drug Dev. Res. 11, 65 (1987)]. Antipsychotic activity with minimal EPS liability has also been noted in schizophrenic patients treated with a potent serotonin 5-HT$_2$ receptor antagonist [R. Axelsson, A. Nilsson, E. Christensson and A. Björk, Psychopharmacol. 104, 287–292 (1991)] or a mixed 5-HT$_2$ and D-2 antagonist [J. F. Castelas et al. Schizophrenia Res. 2, 411–415, (1989)].

U.S. Pat. No. 4,360,673 to Berger et al. describes a series of 5-phenyl-1,3-alkano-1,2,3,4,4a,9b-hexahydropyrido[4,3-b]indoles which are useful as antidepressants but are not stated to be useful as antipsychotics.

U.S. Pat. No. 4,174,453 to Beger et al. discloses a series of trans hexahydropyridoindoles having various utilities including as antipsychotics and anxiolytics.

Welch et al. [J. Med. Chem. 23, 949–952 1980] reported that 4a,9b-trans-8-fluoro-5-(4-fluorophenyl)-2-[4-(4-fluorophenyl)-4-hydroxy-butyl]-2,3,4,4a,9b-hexahydro-1H-pyrido[4,3-b]indole hydrochloride is a potent neuroleptic which acts by blocking dopamine receptors.

Harbert et al. [J. Med. Chem. 23, 635–643 (1980)] described various 5-aryltetrahydro-γ-carbolines which are effective neuroleptics. The mechanism of action of these compounds was thought to be blockade of central dopamine receptors.

Harbert et al. [Mol. Pharm. 17, 38–42 (1980)] also described the conformational requirements for interaction with dopamine receptors for a series of 5-aryltetrahydro-γ-carboline compounds.

Abou-Gharbia et al. [J. Med. Chem. 30, 1818–1823] reported that certain γ-carbolines have antipsychotic activity.

DETAILED DESCRIPTION OF THE INVENTIONS

The compounds of this invention are 5,6,7,8,9,10-hexahydro-7,10-iminocyclohept[b]indoles, 6,7,8,9,10,11-hexahydro-7,11-imino-5H-cyclooct[b]indoles and substituted derivatives which are illustrated by the following Formula I:

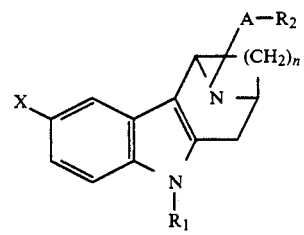

Formula I in which:

X represents hydrogen, fluoro, chloro, or bromo;

R$_1$ represents hydrogen, C$_{1-4}$ alkyl, benzyl, substituted benzyl, substituted phenyl or, provided X, A, or R$_2$ is not hydrogen, phenyl;

A represents hydrogen, C$_{1-6}$ alkyl, or C$_{1-6}$ alkyl wherein one of the methylene carbons is replaced by a carbonyl group; and R$_2$ represents phenyl, substituted phenyl, benzyl, substituted benzyl, phenoxy, substituted phenoxy, diphenyl C$_{1-4}$ alkyl, pyridyl, 2-isoindolinyl, 2-(1,3-dioxoindolinyl), 8-(7,9-dioxo-8-azaspiro[4.5]decanyl), N-(3,4-dichlorophenethyl)-N-methylamino, N-(3,4-dichlorophenylacetyl)-N-methylamino, hydroxyl, or C$_{1-4}$ alkoxy; and n = 2 or 3.

As used in Formula I substituted benzyl, substituted phenyl, and substituted phenoxy are defined respectively as benzyl, phenyl, or phenoxy substituted by halogen, hydroxy, C$_{1-4}$ alkoxy, C$_{1-4}$ alkyl, or any accessible combination thereof; and C$_{1-1'}$ alk(yl) is a straight or branched, saturated or unsaturated alkyl of 1 to 1' carbons.

Preferred compounds are Formula I compounds in which R$_1$ is hydrogen or C$_{1-4}$ alkyl; or R$_1$ is hydrogen, C$_{1-4}$ alkyl, benzyl, or substituted benzyl.

The compounds of this Formula I also may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p- aminobenzoic, glutamic, benzene-sulfonic, hydrochloric, hydrobromic, sulfuric, cyclohexylsulfamic, phosphoric and nitric acids.

The compounds of this invention are racemates which may be resolved into d and l enantiomers. If a second asymmetric center is present in a substituent group, then separable diastereomers are present. It is intended to include all isomers, whether separated or mixtures thereof.

The compounds used in the presently invented pharmaceutical compositions and methods are Formula I compounds wherein X, A, $R_2$, and n are as defined above and $R_1$ is hydrogen, $C_{1-4}$ alkyl, benzyl, substituted benzyl, phenyl, or substituted phenyl.

The compounds of Formula I are generally prepared by the overall sequence indicated as follows:

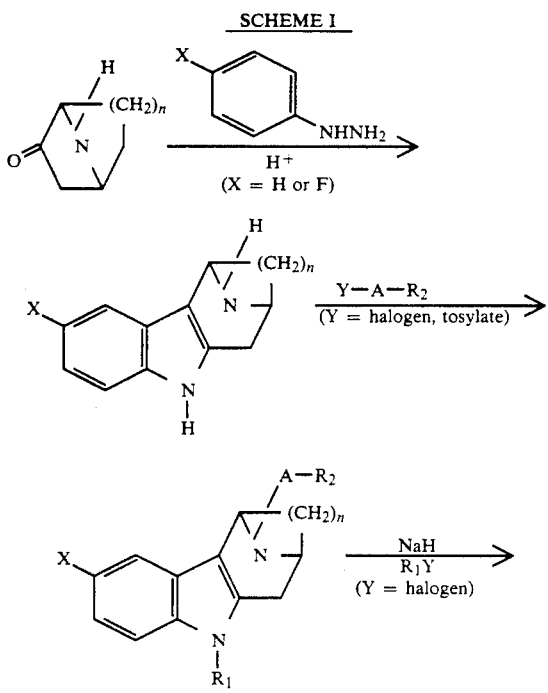

Formula I

Accordingly, phenylhydrazine or 4-fluorophenylhydrazine is condensed with nortropinone or pseudopelletierine (9-azabicyclo-[3.2.1]nonan-3-one) under conditions of the Fischer indole synthesis to afford 5,6,7,8,9,10-hexahydro-7,10-iminocyclohept[b]indole or 6,7,8,9,10,11-hexahydro-7,11-imino-5H-cyclooct[b]indole or the corresponding-2-fluoro derivatives. Alkylation of the basic nitrogen in these compounds with the appropriately substituted alkyl halide or tosylate in dimethylformamide affords the compounds of Formula I wherein $R_1$ is hydrogen. Alternatively, compounds of Formula I may be obtained by acylation of the hexahydro-7,10-iminocyclohept[b]indole or hexahydro-7,11-imino-5H-cyclooct[b]indole followed by reduction of the resulting amide with, for example, lithium aluminum hydride. Compounds of Formula I in which $R_1$ is other than hydrogen or phenyl are prepared by abstraction of the a proton from the indole nitrogen, for example with sodium hydride in dimethylformamide, followed by reaction of the resulting anion with the required alkyl or aralkyl halide. Compounds of Formula I in which $R_1$ is phenyl are prepared by alkylation or acylation/reduction of 5-phenyl-5,6,7,8,9,10-hexahydro-7,10-iminocyclohept-[b]indole (J. G. Berger and P. Tahbaz, U.S. Pat. No. 4,360,673, Nov. 23, 1982) or 5-phenyl-6,7,8,9,10,11-hexahydro-7,11-imino-5H-cyclooct[b]indole as outlined above.

Compounds of Formula I wherein X is chloro or bromo are prepared by substituting the appropriate halogenated analogue of fluorophenylhydrazine in Scheme I, above. Formula I compounds wherein X is at a position other than the 2 position are prepared by substituting the appropriate position analogue for 4-phenylhydrazine in Scheme I.

A variety of evidence [I. Creese, D. R. Burt, and S. H. Snyder, Science, 192, 481 (1976); E. F. Domino and B. Kovacic, Mod. Problems Pharmacopsychiat. 21, 21 (1983); A. J. Stoessl, C. T. Dourish, and S. D. Iverson, Psychopharmacol., 98, 372 (1989)] suggests that EPS associated with traditional antipsychotic agents results from the antagonist activity of these drugs at D-2 dopamine receptors. Recent studies have shown that classical antipsychotic drugs including chlorpromazine and haloperidol, bind to both dopamine D-2 and sigma receptors and that their antipsychotic actions may result from blockade at both of these classes of receptors which are associated with production of psychoses [S. H. Snyder and B. L. Largent, J. Neuropsychol. 1, 7 (1988)]. In animals, antipsychotic-like actions without concomitant effects associated with EPS have been observed with sigma ligands that lack significant affinity for dopamine D-2 receptors [W. Guy, G. Manon and W. H. Wilson, Drug Dev. Res. 3, (1983); D. Taylor and J. Dekleva, Drug Dev. Res. 11, 65 (1987)]. Antipsychotic activity with minimal EPS liability has also been noted in schizophrenic patients treated with a potent serotonin 5-HT$_2$ receptor antagonist [R. Axelsson, A. Nilsson, E. Christensson and A. Björk, Psychopharmacol. 104, 287-292 (1991)]. The compounds of the present invention demonstrate high affinity for sigma and/or serotonin 5-HT$_2$ receptors. In addition, selected compounds of this invention have much higher affinity for DTG vs. (+)-3-PPP sigma sites suggesting selectivity for sigma receptor subpopulations. Thus, these compounds are atypical antipsychotics that are expected to be essentially free of EPS liability. By virtue of their 5-HT$_2$ receptor blocking activity, compounds of this invention are also useful for treating sleep disorders [e.g., K. Adam and I. Oswald, Psychopharmacol. 99, 219-221 (1989)], depression [e.g., G. J. Marek, A. A. Li and L. S. Seiden, J. Pharmacol. Exp. Ther. 250, 52-59 (1989)], neuroleptic-induced akathisia [C. H. Miller, W. W. Fleischhacker, H. Ehrmann and J. M. Kane, Psychopharmacol. Bull., 26, 373-376 (1990)], chronic headache [G. Nappi, G. Sandrini, F. Granella, L. Ruiz, G. Cerutti, F. Facchinetti, F. Blandini and G. C. Manzoni, Headache 30, 439-44 (1990)], ischemic brain injury [H. M. Pappius, J. Neural Trans. Suppl. 29, 49-56 (1990)], hypertension and peripheral vascular disease [R. N.

Brogden and E. M. Sorkin, Drugs 40, 903-949 (1990); T. Hedner and B. Persson, Am. J. Hypertens. 1, 3175-3235 (1988)].

The compositions of this invention are prepared in conventional dosage unit forms by incorporating a compound of Formula I or a pharmaceutically acceptable salt thereof, in a nontoxic amount sufficient to produce the desired therapeutic effect, for example, antipsychotic activity essentially free of EPS in an animal, with a nontoxic pharmaceutical carrier according to accepted procedures. Preferably the compositions will contain the active ingredient in an active but nontoxic amount selected from about 1 mg to about 300 mg., advantageously from about 5 mg to about 100 mg, of active ingredient per dosage unit.

The pharmaceutical carrier employed may be, for example, either a solid or liquid, giving rise to a wide variety of pharmaceutical forms. If a solid pharmaceutical carrier is used, such as lactose, magnesium sterate, terra alba, sucrose, talc, stearic acid, gelatin, agar, pectin, acacia and the like, the composition can be tableted, used as a pharmaceutical powder, placed in a hard gelatin capsule or in the form of a troche or lozenge. The amount of solid carrier will vary widely but preferably will be from about 25 mg to about 1 g. If a liquid pharmaceutical carrier is used, such as syrup, peanut oil, olive oil, sesame oil, water and the like, the composition will be in the form of a soft gelatin capsule, syrup, emulsion or a liquid suspension. Similarly the carrier or diluent may include a time delay material such as glyceryl monostearate or glyceryl distearate alone or with a wax.

Parenteral dosage forms such as for intramuscular administration are obtained by dissolving a water soluble salt of the active medicament in water or saline solution in a concentration such that 1 mL of the solution contains from about 2 mg to about 50 mg of active ingredient. The solution can then be filled into single ampuls or multiple dose vials.

In accordance with the method of the invention a compound of Formula I or a nontoxic acid addition salt thereof is administered internally to an animal in need of therapeutic activity, preferably with a pharmaceutical carrier, in an amount sufficient to produce therapeutic activity, for example, antipsychotic activity essentially free of extrapyramidal symptoms. The active medicament, preferably in a dosage unit, is administered orally or intramuscularly in an active, nontoxic quantity selected preferably from about 1 mg to about 300 mg of the parent chemical of formula I. Advantageously, equal doses will be administered until a desired effect is obtained, such as two or three times a day. The daily dosage is selected from about 2 mg to about 900 mg of active medicament, advantageously from about 10 mg to about 600 mg. When the method described above is carried out, therapeutic activity, e.g. antipsychotic activity can be obtained with EPS less than convention antipsychotics.

The following examples illustrate specific compounds, pharmaceutical compositions and their use in accordance with the method of this invention and as such are not to be considered as limitations thereof.

EXAMPLE 1

5,6,7,8,9,10-Hexahydro-7,10-iminocyclohept[b]indole

Method A, A solution of nortropinone hydrochloride (10.0 g, 61.9 mmol) and phenylhydrazine (7.7 g, 71.2 mmol) in 175 mL of 2-propanol was refluxed for 30 minutes, then it was allowed to cool to room temperature, saturated with hydrogen chloride, and heated under reflux for an additional 10 hours. The resulting solution was concentrated under reduced pressure to give a dark residue which was dissolved in methanol. Amberlite IRA-400 resin (pre-washed with methanol) was added until the pH exceeded 10. The mixture was filtered and the filter cake was washed with hot methanol to complete removal of the product from the resin. After the filtrate was treated with decolorizing carbon, it was filtered through a pad a diatomaceous earth and concentrated in vacuo. The residue was suspended in 50 mL of methylene chloride and the mixture was held at $-5°$ C. for 24 hours. Filtration afforded 8.4 g (69%) of 5,6,7,8,9,10-hexahydro-7,10-iminocyclohept[b]indole which was converted into a hydrogen fumarate in ethanol, mp 208°-209° C. (dec); NMR (DMSO-d6) d 1.63 (1H, m), 1.90 (1H, m), 2.15-2.19 (2H, m), 2.68 (1H, d, J=16, 4 Hz), 3.31 (1H, dd, J=16.6, 4 7.28 (1H, d, J=8 Hz), 7.46 (1H, d, J=8 Hz), 11.10 (1H, s).

Anal. ($C_{13}H_{14}N_2.0.5C_4H_4O_4$).

Method B. A stirred solution of 5.0 g (30.96 mmol) of nortropinone hydrochloride and 4.6 g (31.89 mmol) of phenylhydrazine hydrochloride in 20 mL of ethanol was heated at reflux for 2.5 hours. After slow dropwise addition of 5 mL of concentrated sulfuric acid, the reaction mixture was stirred and refluxed for an additional 16 hours, and then it was added to a 50 mL of ethanol and sufficient IRA-400 resin was added to bring the mixture to pH 10. Decolorizing carbon (10 g) was added and the mixture was stirred at ambient temperature for 30 minutes. The mixture was filtered through a pad of diatomaceous earth. After the filter cake was washed several times with warm ethanol, the filtrates were combined and concentrated. The residue was chromatographed on silica gel using methylene chloride: methanol: aqueous ammonium hydroxide/91.5: 7.5: 1.0 to afford 3.19 g (52%) of 5,6,7,8,9,10-hexahydro-7,10-iminocyclohept[b]indole identical with that obtained by Method A.

11-(4-Phenoxybutyl)-5,6,7,8,9,10-hexahydro-7,10-iminocyclohept[b]indole

A mixture of 694 mg (3.03 mmole) of 1-bromo-4-phenoxybutane, 400 mg (2.02 mmol) of 5,6,7,8,9,10-hexahydro-7,10-iminocyclohept[b]indole, 418 mg (3.03 mmol) of potassium carbonate and 5 mL of dimethylformamide was stirred at 60° C. for 4 hours. After being cooled to 25° C., the mixture was diluted with 200 mL of ethyl acetate and 30 mL of water. The organic layer was separated, washed with brine, dried over sodium sulfate and concentrated in vacuo. Flash chromatography (methylene chloride: methanol/95:1) afforded 610 mg (91%) of the product, which was converted to a fumarate, mp 135°-138° C., after recrystallization from THF.

This general procedure utilizing 1-iodopropane, 4-bromo-1-butene, benzyl bromide, 1-bromo-2-phenylethane, 1tosyl-2-(3,4-dichlorophenyl)ethane, 1-bromo-3-phenylpropane, 1-bromo-4-phenylbutane, 2-bromo-4-phenylbutane, 1-bromo-5-phenylpentane, cinnamyl bromide, 1-bromo-3,3-diphenylpropane, 1-bromo-2-phenoxyethane, 1-bromo-2-(4-chlorophenoxy)ethane, 1-bromo-3-phenoxypropane, 1-chloro-3-(4-fluorophenoxy)propane, 1-chloro-4-(4-fluorophenyl)-4-oxobutane, and 8-(4-chlorobutyl)-8-azaspiro[4.5]decane-7,9-dione, 1-bromo-4-(4-fluorophenyl)butane, 1- chloro-5-(4-fluorophenyl)-5-oxopentane, and 1-chloro-4-phenyl-4-oxobutane to alkylate (a catalytic amount of potassium iodide was added to the reaction mixture when chlorides or tosylates were used) 5,6,7,8,9,10-hexahydro-7,10-iminocyclohept[b]indole afforded the following compounds:

11-(n-propyl)-5,6,7,8,9,10-hexahydro-7,10-iminocyclohept[b]indole hydrogen oxalate, mp 187°-188° C., dec. (from acetone);

11-(3-butenyl)-5,6,7,8,9,10-hexahydro-7,10-iminocyclohept[b]-indole hydrogen oxalate, mp 179.5°-182° C. (from ethanol);

11-benzyl-5,6,7,8,9,10-hexahydro-7,10-iminocyclohept[b]indole hemihydrate, mp 193°-194.5° C. (trituration with hexane);

11-(2-phenylethyl)-5,6,7,8,9,10-hexahydro-7,10-iminocyclohept[b]indole hydrogen oxalate, mp 176°-181° C. dec. (trituration with ether);

11-[2-(3,4-dichlorophenyl)ethyl]-5,6,7,8,9,10-hexahydro-7,10-iminocyclohept[b]indole hydrogen oxalate, mp 183.5°-184.5° C. dec. (from acetone);

11-(3-phenylpropyl)-5,6,7,8,9,10-hexahydro-7,10-iminocyclo-hept[b]indole hydrogen oxalate, mp 149°-152° C. (from THF);

11-(4-phenylbutyl)-5,6,7,8,9,10-hexahydro-7,10-iminocyclohept[b]indole hydrochloride hemihydrate;

11-(4-phenyl-2-butyl)-5,6,7,8,9,10-hexahydro-7,10-iminocyclo-hept[b]indole (TLC, silica, methylene chloride:methanol:concentrated ammonium hydroxide/90:9:1, $R_f=0.25$) hydrogen oxalate hemihydrate, my 200°-201° C. (from ethanol);

11-(4-phenyl-2-butyl)-5,6,7,8,9,10-hexahydro-7,10-iminocyclo-hept[b]indole (TLC, silica, methylene chloride:methanol:concentrated ammonium hydroxide/90:9:1, $R_f=0.31$) hydrogen oxalate hemihydrate mp 194°-195° C. (from ethanol);

11-(5-phenylpentyl)-5,6,7,8,9,10-hexahydro-7,10-iminocyclo-hept[b]indole hydrogen oxalate, mp 106°-109° C. (from THF);

11-cinnamyl-5,6,7,8,9,10-hexahydro-7,10-iminocyclohept-[b]indole, 211°-212° C. (from acetone);

11-(3,3-diphenylpropyl)-5,6,7,8,9,10-hexahydro-7,10-iminocyclohept[b]indole hydrochloride, mp 202°-203° C. (from ethyl acetate);

11-(2-phenoxyethyl)-5,6,7,8,9,10-hexahydro-7,10-iminocyclo-hept[b]indole hydrogen oxalate, mp 169°-170.5° C. (from THF);

11-[2-(4-chlorophenoxy)ethyl]-5,6,7,8,9,10-hexahydro-7,10-iminocyclohept[b]indole hydrogen fumarate, mp 198°-199° C. dec. (from THF);

11-(3-phenoxypropyl)-5,6,7,8,9,10-hexahydro-7,10-iminocyclo-hept[b]indole hydrogen oxalate, mp 164°-167° C. dec. (from THF);

11-[3-(4-fluorophenoxy)propyl]-5,6,7,8,9,10-hexahydro-7,10-iminocyclohept[b]indole hydrogen oxalate mp 174°-175.5° C. (from ethanol);

11-[4-(4-fluorophenyl)-4-oxobutyl]-5,6,7,8,9,10-hexahydro-7,10-iminocyclohept[b]indole, mp 166°-168° C. (from ether);

11-[4-(8-azaspiro[4.5]decane-7,9-dione-8-yl)butyl]-5,6,7,8,9,10-hexahydro-7,10-iminocyclohept[b]indole hemihydrate, mp 149°-152° C. (from ethyl acetate) also known as 11-{8-(7,9-dioxo-8-azaspiro[4.5-]decanyl)}-5,6,7,8,9,10-hexahydro-7,10-iminocyclohept[b]indole;

11-[4-(4-fluorophenyl)butyl]-5,6,7,8,9,10-hexahydro-7,10-iminocyclohept[b]indole hydrogen oxalate, mp 120°-121° C. (from hexane);

11-[5-(4-fluorophenyl)-5-oxopentyl]-5,6,7,8,9,10-hexahydro-7,10-iminocyclohept[b]indole hydrogen oxalate hydrate, mp 92°-95° C. (from ether); and 11-(4-phenyl-4-oxobutyl)-5,6,7,8,9,10-hexahydro-7,10-iminocyclohept[b]indole hydrogen oxalate, mp 156°-158° C. (from acetone).

EXAMPLE 2

5-Phenyl-5,6,7,8,9,10-hexahydro-7,10-iminocyclohept[b]indole hydrochloride

Substituting N,N-diphenylhydrazine for phenylhydrazine in the Fischer indole synthesis described in Example 1, Method A, gave the colorless, crystalline product as a hemihydrate, mp 262°-264° C. dec. (from water). Anal. $C_{19}H_{18}N_2.HCl.0.5H_2O$.

11-[4-(4-Fluorophenyl)-4-oxobutyl]-5-phenyl-5,6,7,8,9,10-hexahydro-7,10-iminocyclohept[b]indole This compound was prepared by alkylation of 5-phenyl-5,6,7,8,9,10-hexahydro-7,10-iminocyclohept[b]indole with 1-chloro-4-(4-fluorophenyl)-4-oxobutane in the presence of diisopropylethylamine according to the alkylation procedure described in Example 1 to give a crystalline hydrogen oxalate, mp 183°-184° C. dec. (from ethyl acetate). Anal. $C_{29}H_{27}FN_2O.C_2H_2O_4$.

EXAMPLE 3

11-Methyl-5,6,7,8,9,10-Hexahydro-7,10-iminocyclohept[b]indole

This compound was prepared from phenylhydrazine and tropinone by the procedure described in Example 1, Method A: colorless crystals, mp 158°-161° C. (from ether).

EXAMPLE 4

2-Fluoro-5,6,7,8,9,10-hexahydro-7,10-iminocyclohept[b]indole

This compound was prepared from 4-fluorophenylhydrazine and nortropinone by the procedures described in Example 1, Method A (75% yield) or Method B (60% yield). A hydrogen fumarate hemihydrate was prepared in ethanol, mp 145° C. dec; NMR (DMSO-D$_6$) d 1.71-1.78. (1H, m), 1.95-1.98 (1H, m), 2.19-2.22 (2H, m), 2.79 (1H, d, J=16.8 Hz), 3.36 (1H, dd, J-16.9, 4.4 Hz), 4.33 (1H, bs), 5.00 (1H, d, J=4.2 Hz), 6.43 (2H, s), 6.84-6.91 (1H, m), 7.28=7.36 (2H, m), 11.30 (1H, s). Anal. ($C_{13}H_{13}N_2F.C_4H_4O_4.0.5H_2O$).

2-Fluoro-11-(3-hydroxypropyl)-5,6,7,8,9,10-hexahydro-7,10-iminocyclohept[b]indole This compound was prepared by alkylation of 2-fluoro-5,6,7,8,9,10-hexahydro-7,10-iminocyclohept[b]indole with 3-bromopropanol by alkylation procedure detailed in Example 1. The base was characterized as its hydrogen oxalate salt, mp 155°-160° C. (from 2-propanol).

This general procedure utilizing 2-bromoethanol, benzyl bromide, 2-iodobenzyl bromide, 1-bromo-4-phenylbutane, 1-bromo-3-(3-pyridyl)propane hydrobromide, and 1-chloro-4-(4-fluorophenyl)-4-oxobutane to alkylate 2-fluoro-5,6,7,8,9,10-hexahydro-7,10-iminocyclohept[b]indole (a catalytic amount of potassium iodide was added for alkylation with the alkyl chloride) afforded:

2-fluoro-11-(2-hydroxyethyl)-5,6,7,8,9,10-hexahydro-7,10-iminocyclohept[b]indole hydrochloride hemihydrate, mp 165°–170° C. (trituration with ether);

2-fluoro-11-(2-iodobenzyl)-5,6,7,8,9,10-hexahydro-7,10-iminocyclohept[b]indole hydrogen oxalate hemi-2-propanolate, mp 132°–138° C. (from 2-propanol);

2-fluoro-11-(4-phenylbutyl)-5,6,7,8,9,10-hexahydro-7,10-iminocyclohept[b]indole hydrogen oxalate, mp 161°–161.5° C. (from THF-ethyl acetate);

2-fluoro-11-[4-(4-fluorophenyl)-4-oxobutyl]-5,6,7,8,9,10-hexahydro-7,10-iminocyclohept[b]indole hydrogen oxalate hemihydrate, mp 128°–130° C. (from acetone); and 2-fluoro-11-(3-pyridylpropyl)-5,6,7,8,9,10-hexahydro-7,10-iminocyclohept[b]indole hydrogen fumarate, mp 154°–156° C. (from acetone).

EXAMPLE 5

11-(4-Phenylbutyl)-5-(2-propyl)-5,6,7,8,9,10-hexahydro-7,10-iminocyclohept[b]indole A mixture of 670 mg (2.03 mmol) of 11-(4-phenylbutyl)-5,6,7,8,9,10-hexahydro-7,10-iminocyclohept[b]indole, 300 mg (12.5 mmol) of sodium hydride and 20 mL of dimethylformamide was stirred at ambient temperature for 30 minutes. After 744 mg (6.1 mmol) of 2-bromopropane was added, the mixture was stirred for an additional 4 hours. To the reaction mixture was added 200 mL of ethyl acetate and 50 mL of brine. The organic layer was separated, dried over sodium sulfate, and concentrated. The residue was chromatographed (silica, methylene chloride:methanol/95:5) to give 440 mg of an oil which was treated with an excess of oxalic acid in acetone to give colorless crystals, mp 178°–180° C. Anal. ($C_{26}H_{32}N_2.C_2H_2O_4$).

Replacement of 2-bromopropane in this procedure with methyl iodide and benzyl bromide afforded:

5-methyl-11-(4-phenylbutyl)-5,6,7,8,9,10-hexahydro-7,10-iminocyclohept[b]indole hydrogen oxalate, mp 170°–171° C. (from 2-propanol); and 5-benzyl-11-(4-phenylbutyl)-5,6,7,8,9,10-hexahydro-7,10-iminocyclohept[b]indole hydrogen oxalate, mp 181°–183° C. (from 2-propanol).

Using 11-(2-phenylethyl)-5,6,7,8,9,10-hexahydro-7,10-iminocyclohept[b]indole and benzyl bromide in the procedure of this example afforded:

5-benzyl-11-(2-phenylethyl)-5,6,7,8,9,10-hexahydro-7,10-iminocyclohept[b]indole hydrogen oxalate.

EXAMPLE 6

2-Fluoro-11-(3-phthalimidopropyl)-5,6,7,8,9,10-hexahydro-7,10-iminocyclohept[b]indole A mixture of 630 mg (2.31 mmol) of 2-fluoro-11-(3-hydroxypropyl)-5,6,7,8,9,10-hexahydro-7,10-iminocyclohept[b]indole, 665 mg (2.54 mmol) of triphenylphosphine and 442 mg (2.54 mmol) of diethyl azadicarboxylate in 20 mL of THF was stirred at 25° C. for 18 hours. The reaction mixture was diluted with 200 mL of methylene chloride and 60 mL of water. The organic layer was separated, dried over sodium sulfate, and concentrated to give an oily residue. Flash chromatography of the residue (silica, methylene chloride:methanol/95:5) afforded 760 mg (82%) of product which was treated with excess oxalic acid in methanol to give a hydrogen oxalate, mp 155°–160° C. Anal. ($C_{24}H_{22}FN_3O_2.C_2H_2O_4$).

Substituting 11-(2-hydroxyethyl)-5,6,7,8,9,10-hexahydro-7,10-iminocyclohept[b]indole in the procedure of this example gave:

11-(2-phthalimidoethyl)-5,6,7,8,9,10-hexahydro-7,10-iminocyclohept[b]indole hydrogen oxalate, mp 163°–165° C. (from THF).

EXAMPLE 7

2-Fluoro-11-[3-(2-isoindolinyl)propyl]-5,6,7,8,9,10-hexahydro-7,10-iminocyclohept[b]indole To a solution of 390 mg (0.1 mmol) of 2-fluoro-11-(3-phthalimidopropyl)-5,6,7,8,9,10-hexahydro-7,10-iminocyclohept[b]indole in 10 mL of THF was added dropwise 4.5 mL of 1M lithium aluminum hydride in THF. After the reaction mixture was stirred and refluxed for 3 hours, it was cooled to 10° C. and water (0.2 mL), 2.5N sodium hydroxide (0.2 mL) and water (0.2 mL) were sequentially added dropwise. The resulting mixture was filtered and the filter cake was washed thoroughly with THF. The combined filtrates were concentrated and the residue was flash chromatographed (silica, methylene chloride: methanol: concentrated ammonium hydroxide/94:5:1) to give 320 mg (88%) of product which was treated with excess oxalic acid in ethanol to give colorless crystals, mp 162°–165° C. (from ethanol).

Similar lithium aluminum hydride reduction of 11-(2-phthalimidoethyl)-5,6,7,8,9,10-hexahydro-7,10-iminocyclohept[b]indole afforded:

11-[2-(2-isoindolinyl)ethyl]-5,6,7,8,9,10-hexahydro-7,10-iminocyclohept[b]indole hydrogen oxalate, mp 154°–158° C. (from ethanol).

EXAMPLE 8

11-[2-(3,4-Dichlorophenoxy)acetyl]-5,6,7,8,9,10-hexahydro-7,10-iminocyclohept[b]indole To a suspension of 1.0 g (5.04 mmol) of 5,6,7,8,9,10-hexahydro-7,10-iminocyclohept[b]indole in 10 mL of methylene chloride was added 1.45 g (6.05 mmol) of 3,4-dichlorophenoxyacetyl chloride in 10 mL of methylene chloride. After being stirred for 1 hour the reaction mixture was poured into an aqueous solution of sodium bicarbonate. The organic layer was separated and the aqueous layer was extracted with 2-25 mL portions of methylene chloride. The combined organic extracts were dried and concentrated. Flash chromatography of the residue (silica, ethyl acetate: hexane/50:50) gave 1.37 g (68%) of crystalline product, mp 198.5°–199.5° C., after recrystallization from ethyl acetate.

11-[2-(3,4-Dichlorophenoxy)ethyl]-5,6,7,8,9,10-hexahydro-7,10-iminocyclohept[b]indole To a solution of 500 mg (1.25 mmol) of 11-[2-(3,4-dichlorophenoxy)acetyl]-5,6,7,8,9,10-hexahydro-7,10-iminocyclohept[b]indole in 6 mL of THF was added 8 mL of 0.66M aluminum hydride in THF, prepared by *cautiously* adding 0.53 mL of concentrated sulfuric acid to 30 mL of 0.67M lithium aluminum hydride. The reaction mixture was stirred for 30 minutes, and then it was poured into 30 mL of 2.5N sodium hydroxide. The mixture was extracted with ethyl acetate. The combined organic extracts were dried over sodium sulfate and concentrated. A solution of the residue in acetone was treated with excess fumaric acid to give 280 mg of colorless, crystalline fumarate, mp 182°–183° C.

EXAMPLE 9

11-[2-(tert-Butoxycarbonylamino)acetyl]-5,6,7,8,9,10-hexahydro-7,10-iminocyclohept[b]indole To a stirred solution of 1.0 g (5.04 mmol) of 5,6,7,8,9,10-hexahydro-7,10-iminocyclohept[b]indole in 20 mL of methylene chloride at 0° C. was added 1.0 g (5.71 mmol) of N-(tert-butoxycarbonyl)glycine, 1.09 g (5.71 mmol) of 1-ethyl-3-[3-(dimethylamino)propyl]carbodiimide hydrochloride and 40 mg of 4-dimethylaminopyridine. Stirring was continued for 16 hours as the mixture was allowed to slowly come to ambient temperature. To the reaction mixture was added 150 mL of ethyl acetate and 40 mL of water. After the mixture was stirred for 15 minutes, the organic layer was separated, washed with brine, dried over magnesium sulfate and concentrated. Chromatography (silica, ethyl acetate: hexane/50:50) afforded 1.38 g (77%) of colorless crystals, mp 213.5°–214.5° C.

11-[2-(Methylamino)ethyl]-5,6,7,8,9,10-hexahydro-7,10-iminocyclohept[b]indole Lithium aluminum hydride reduction of 11-[2-(3,4-dichlorophenoxy)ethyl]-5,6,7,8,9,10-hexahydro-7,10-iminocyclohept[b]indole by the general procedure described in Example 6 afforded an oily product which was characterized by NMR (CDCl$_3$).

11-{N-[2-(3,4-Dichlorophenyl)ethyl]-2-(methylamino)ethyl}-5,6,7,8,9,10-hexahydro-7,10-iminocyclohept[b]indole Alkylation of 11-[2-(methylamino)ethyl]-5,6,7,8,9,10-hexahydro-7,10-iminocyclohept[b]indole with 1-tosyl-2-(3,4-dichlorophenyl)ethane was carried out by the general alkylation procedure described in Example 1 to give the product which was characterized as a colorless crystalline dioxalate, mp 137°–139° C. dec (from THF). Anal. (C$_{24}$H$_{27}$Cl$_2$N$_3$·2C$_2$H$_2$O$_4$).

EXAMPLE 10

11-{N-[2-(3,4-Dichlorophenyl)acetyl]-2-(methylamino)ethyl}-5,6,7,8,9,10-hexahydro-7,10-iminocyclohept[b]indole 11-{N-[2-(3,4-Dichlorophenyl)ethyl]-2-(methylamino)ethyl}-5,6,7,8,9,10-hexahydro-7,10-iminocyclohept[b]indole was acylated with 3,4-dichlorophenoxyacetyl chloride by the general procedure described in Example 7 to give the product which was characterized as a crystalline hydrogen oxalate mp 132°–133° C. (from ethyl acetate). Anal. (C$_{24}$H$_{25}$Cl$_2$N$_3$·C$_2$H$_2$O$_4$).

EXAMPLE 11

9-(2,2,2-Trichlorocarbethoxy)-9-azabicyclo[3.3.1]nonan-3-one

To a solution of pseudopelletierine (52 g, 0.34 mol) in toluene (220 mL) at 50° C. was added anhydrous potassium carbonate (1.0 g), followed by the slow addition of trichloroethylchloroformate (79 g, 0.37 mol). After addition was completed (30 minutes), triethylamine (10 mL) was added. The reaction was allowed to cool to room temperature and stirred for 18 hours. The reaction mixture was diluted with ethyl acetate (300 mL) and 1N hydrochloric acid (200 mL). After the organic layer was washed with 1N hydrochloric acid (100 mL), it was washed with aqueous 10% sodium hydroxide (100 mL). The organic layer was dried over anhydrous sodium sulfate, filtered and concentrated to afford a beige solid which was triturated with hexane (300 mL) to afford 81.4 g of crystalline solid (76% yield); mp 95°–96° C. after recrystallization from ethyl acetate-hexane. Anal. (C$_{11}$H$_{14}$Cl$_3$NO$_3$).

9-Azabicyclo[3.3.1]nonan-3-one Hydrochloride

To suspension of zinc (67.2 g, 1.03 g-atom) in glacial acetic acid (40 mL) at 65° C. was slowly added a solution of 9-(2,2,2-trichlorocarbethoxy)-9-azabicyclo[3.3.1]nonan-3-one (80.9 g, 0.26 mol) in glacial acetic acid (120 mL) over 1 hour. An additional 40 mL of glacial acetic acid was used to rinse the addition funnel and the reaction was stirred at 65° C. until no further gas evolution was observed. The reaction was allowed to cool slightly and water (40 mL) was added to dissolve the organic acetate salts. The reaction was filtered and solvent was removed under vacuum. The resultant orange oil was slowly added to concentrated ammonium hydroxide (80 mL) using water (80 mL) to aid in the transfer. An additional 80 mL of concentrated ammonium hdroxide was added, followed by the addition of a solution of 31 g of sodium hydroxide in 155 mL of water. The solution was extracted with methylene chloride (6×300 mL), dried over anhydrous sodium sulfate, filtered, and concentrated to an oil. The oil was dissolved in 200 mL of ether and the solution was slowly added to 1N hydrogen chloride in ether (310 mL) while vigorously stirring to give 38.7 g (86% yield) of a colorless hydrochloride, m.p. 216°–219° C. after trituration with ether and drying. Anal. (C$_8$H$_{14}$ClNO).

6,7,8,9,10,11-Hexahydro-7,11-imino-5H-cyclooct[b]indole

This compound was prepared from 9-azabicyclo[3.3.1]nonan-3-one hydrochloride and phenylhydrazine by Fischer indole synthesis as described in Example 1, Method A, to give colorless crystals, mp 198°–203° C. (from methylene chloride; it was also converted to a hydrogen oxalate hemihydrate, mp 68°–72° C. (from ethanol-ether).

12-[5-(4-Fluorophenyl)-5-oxobutyl]-6,7,8,9,10,11-hexahydro-7,11-imino-5H-cyclooct[b]indole Hydrogen Oxalate Hemihydrate This compound was prepared by alkylation of 6,7,8,9,10,11-hexahydro-7,11-imino-5H-cyclooct[b]indole with 1-chloro-4-(4-fluorophenyl)-4-oxobutane using the procedure described in Example 1 to give colorless crystals, mp 104°–108° C. (from ethanol-ether).

This general procedure utilizing 1-bromo-4-(4-fluorophenyl)butane, 1-bromo-4-phenylbutane, 1,1-di(4-fluorophenyl)-4-bromobutene and 1-bromo-5-(4-fluorophenyl)-5-oxopentane to alkylate 6,7,8,9,10,11-hexahydro-7,11-imino-5H-cyclooct[b]indole afforded:

12-[4-(4-fluorophenyl)butyl]-6,7,8,9,10,11-hexahydro-7,11-imino-5H-cyclooct[b]indole hydrogen oxalate, mp 156°–160° C. (from ethanol-ether);

12-(4-phenylbutyl)-6,7,8,9,10,11-hexahydro-7,11-imino-5H-cyclooct[b]indole hydrogen oxalate, mp 58°–62° C. (from ethanol-ether);

12-[1,1-di(4-fluorophenyl)butenyl]-6,7,8,9,10,11-hexahydro-7,11-imino-5H-cyclooct[b]indole hydrogen oxalate, mp 120°–123° C. (from ethanol-ether); and 12-[5-(4-fluorophenyl)-5-oxopentyl]-6,7,8,9,10,11-hexahydro-7,11-imino 5H-cyclooct[b]indole hydrogen oxalate, mp 56°–59° C. (from ethanol-ether).

EXAMPLE 12

5-Fluoro-6,7,8,9,10,11-hexahydro-7,11-iminocyclooct[b]indole

This compound was prepared from 9-azabicyclo[3.3.1]nonan-3-one hydrochloride and 4-fluorophenylhydrazine by the Fischer indole synthesis as described in Example 1, Method A. The product was obtained as yellow crystals (74% yield), mp 200°–201° C. (from methylene chloride).

2-Fluoro-12-[4-(4-fluorophenyl-4-oxobutyl]-6,7,8,9,10,11-hexahydro-7,11-imino-5H-cyclooct[b]indole Hydrogen Oxalate This compound was prepared by alkylation of 2-fluoro-6,7,8,9,10,11-hexahydro-7,11-iminocyclooct[b]indole with 1-chloro-4-(4-fluorophenyl)-4-oxobutane, ethylene ketal by the general procedure described in Example 1. The ketal alkylation product was hydrolyzed to the ketone using concentrated hydrochloric acid: methanol (1:30). After the mixture was refluxed for one hour it was concentrated. The residue was dissolved in methanol and an equivalent of oxalic acid was added. Addition of ether to the cloud point followed by cooling afforded colorless crystals, mp 120°–124° C. after recrystallization from ethanol-ether. Anal. ($C_{24}H_{24}FN_2 \cdot C_2H_2O_4$).

This general procedure utilizing 1-bromo-4-(4-fluorophenyl)butane, 1-bromo-4-phenylbutane and 1,1-di(4-fluorophenyl)-4-bromobutene to alkylate 5-fluoro-6,7,8,9,10,11-hexahydro-7,11-iminocyclooct[b]indole afforded:

2-fluoro-12-(4-fluorophenybutyl)-6,7,8,9,10,11-hexahydro-7,11-imino-5H-cyclooct[b]indole hydrogen oxalate, mp 175°–176° C. (from ethanol-ether);

2-fluoro-12-(4-phenylbutyl)-6,7,8,9,10,11-hexahydro-7,11-imino-5H-cyclooct[b]indole hydrogen oxalate, mp 105°–111° C. (ether trituration); and 12-[1,1-di(4-fluorophenyl)butenyl]-6,7,8,9,10,11-hexahydro-7,11-imino-5H-cyclooct[b]indole hydrogen oxalate, mp 119°–123° C. (ether trituration).

EXAMPLE 13

In Vitro Sigma Receptor Binding

Sigma ligand binding was studied as described by Karbon et al. [E. W. Karbon, K. Naper and M. J. Pontecorvo, Eur. J. Pharmacol., 193, 21–27 (1991)] using [$^3$H]DTG (S.A.=39.1 Ci/mmol) and [$^3$H](+)PPP (S.A.=108 Ci/mmol) as tracers. For both assays frozen guinea pig brains (PelFreez Biologicals, Rogers, AK) were thawed and homogenized in 10 volumes (w/v) of ice cold 0.32M sucrose using 10 strokes of a motor-driven glass-fitted teflon pestle adjusted to 600 rpm. The homogenate was centrifuged (4° C.) at 900×g for 10 minutes and the resultant supernatant collected and centrifuged at 22,000×g for 20 minutes. The pellet obtained from the centrifugation was resuspended in 10 volumes of 50 mM Tris HCl (pH 7.4, 25° C.) and incubated for 30 minutes at 37° C. Following the preincubation, the homogenate was centrifuted at 22,000×g for 20 minutes and the final pellet was resuspended in buffer to a protein concentration of 0.5–1.0 mg/mL for use in the assay.

Binding reactions were initiated by the addition of tissue (800 μL) to tubes containing assay buffer, the radioligand (final concentration 1–3 nM) and the compound of interest. Haloperidol (10 μM) and (+)-3-PPP (10 μM) were used to determine the levels of specific [$^3$H]DTG and [$^3$H](+)PPP binding, respectively. Final assay volume was 1 mL. Reactions were allowed to proceed for 45 minutes at 25° C. and terminated by rapid filtration over Whatman GF/B filters which were washed 3 times with 5 mL of cold buffer. Radioactivity trapped on the filters was determined using routine methods. For determination of equilibrium dissociation constants ($K_D$), a fixed concentration of radioligand was incubated in the presence of unlabeled ligand ranging in concentration between 0.5–10,000 nM. The concentration of test compound causing 50% inhibition of radioligand binding ($IC_{50}$) was determined from concentration-response curves in which a number of concentrations of test comound were examined. All assays were performed using triplicate determinations. For comparison purposes, $IC_{50}$ values are reported rather than $K_i$ values.

Results are reported in Table 1.

EXAMPLE 14

In Vitro Serotonin (5-HT$_2$) Receptor Binding

The potency of compounds to inhibit the specific binding of [$^3$H]ketanserin (84.2 Ci/mM) to serotonin 5-HT$_2$ receptors was determined as detailed previously [J. E. Leysen, C. J. E. Niemegers, J. M. Van Neuten and P. M. Laduron, Mol. Pharmacol., 21, 301–314 (1982)]. Rat cortical synaptosomal membranes were prepared on the day of assay. Animals were sacrified by decapitation, the frontal cortex was removed and homogenized in 10 volumes (w/v) of ice-cold 0.32M sucrose using a motor driven teflon pestle fitted to a glass tube. The synaptosomal pellet was suspended in 50 mM Tris HCl (pH 7.6 at 25° C.) to a concentration of 7.5 mg original wet weight/mL. For the binding reaction, 400 μL of this tissue suspension was added to polypropylene tubes containing 50 mM Tris HCl and [$^3$H]ketanserin (final concentration of 1 nM) in a final assay volume of 0.5 mL. Following a 15 minute incubation at 37° C., the binding reaction was terminated by rapid vacuum filtration over Whatman GF/B filters (presoaked in 0.1% PEI) followed by 3×4 mL washes with ice cold 50 mM Tris HCl. Nonspecific binding was assessed in the presence of 10 μM methysergide. All incubations were performed in triplicate. $IC_{50}$ values were determined using log logit analysis. $K_i$ values were determined using the Cheng-Prusoff equation, $K_i = IC_{50}/(1+L/K_D)$, where $K_D=2$ nM.

Results are reported in Table 1.

EXAMPLE 15

In Vitro Dopamine (D-2) Receptor Binding

The affinity of compounds for dopamine (D-2) receptors was determined according to the method of Imafuku [J. Imatuku, Brain Res. 402, 331–338 (1987)] using [$^3$H]sulpiride (S.A.=61.8 Ci/mmol). On the day of assay, rats were sacrificed by decapitation, the corpus striatum was dissected and homogenized in 20 volumes of ice-cold 50 mM Tris HCl (pH 7.5, 25° C.). The homogenate was centrifuged (4° C.) at 48,000×g for 10 minutes and the resulting pellet was resuspended in 20 volumes of fresh buffer and recentrifuged. The final pellet was resuspended in fresh buffer containing 100 mM NaCl to a tissue concentration of 3.75 mg wet weight/mL. A portion of the suspension (800 μL) was added in triplicate to tubes containing 3 nM [³H]sulpiride and the test compound. The final assay volume was 1 mL; haloperidol (10 μM) was used to determine nonspecific binding. Following a 60 minute incubation at 25° C., the reactions were terminated by rapid filtration over Whatman GF/B filters which had been pretreated in a solution of 0.3% (w/v) of aqueous polyethylenimine. Filters were washed three times using 5 mL of ice-cold buffer and processed using standard procedures to determine radioactivity. $IC_{50}$ values were obtained from concentration-response curves in which a number of concentrations of test compound were examined. $K_i$ values were determined using the Cheng-Prusoff equation.

Results are reported in Table 1.

TABLE 1

In Vitro Sigma ([³H]DTG, [³H] (+)-3-PPP), Serotonin
5-HT₂ ([³H] ketanserin), and Dopamine D-2 ([³H] sulpiride) Binding

| | | | Formula 1 | | | Sigma IC₅₀, nM | | Dopamine D-2 Ki, μM | Serotonin 5-HT₂ Ki, nM |
|---|---|---|---|---|---|---|---|---|---|
| Example | X | R₁ | A | R₂ | n | [³H] DTG | [³H] (+)-3-PPP | sulpiride | ketanserin |
| 1 | H | H | — | H | 2 | 5000 | 2180 | 100 | 0.2% @ 1 μM |
| 4 | F | H | — | H | 2 | 1473 ± 83 | 1212 ± 178 | 36.6 | 28.2% @ 1 μM |
| 3 | H | H | — | CH₃ | 2 | 2650 ± 1150 | 2005 ± 1095 | 16.7 ± 6.0 | 26.4% @ 1 μM |
| 1 | H | H | (CH₂)₂ | CH₃ | 2 | 1084 ± 43 | 1276 ± 724 | 14.4 ± 4.4 | — |
| 1 | H | H | (CH₂)₂ | CH=CH₂ | 2 | 683 ± 402 | 1763 ± 432 | 0.71 | 12.3% @ 1 μM |
| 1 | H | H | CH₂ | Ph | 2 | 345 ± 85 | 2750 ± 550 | 3.65 ± 0.25 | 22.4% @ 1 μM |
| 4 | F | H | CH₂ | Ph | 2 | 86 ± 14 | 908 ± 222 | 3.74 | 3.3% @ 1 μM |
| 1 | H | H | CH₂ | 2-IPh | 2 | 3044 ± 574 | >10000 | 5.31 ± 0.98 | 0% @ 1 μM |
| 1 | H | H | (CH₂)₂ | Ph | 2 | 234 ± 6 | 1280 ± 300 | 0.84 | 8.8% @ 1 μM |
| 5 | H | H | (CH₂)₂ | 2-IPh | 2 | 482 ± 72 | 305 | 1.62 | 23.3% @ 1 μM |
| 5 | H | H | (CH₂)₂ | 3,4-Cl₂Ph | 2 | 702 ± 66 | >10000 | 3.43 | 6.7% @ 1 μM |
| 1 | H | H | (CH₂)₃ | Ph | 2 | 81 ± 13 | 368 ± 60 | 2.60 | 106 |
| 1 | H | H | (CH₂)₄ | Ph | 2 | 24 ± 6 | 112 ± 50 | 0.72 | 56.5 |
| 4 | F | H | (CH₂)₄ | Ph | 2 | 38 ± 4 | 178 ± 17 | 0.77 ± 0.21 | 74 |
| 5 | H | Bn | (CH₂)₄ | Ph | 2 | 267 ± 87 | 396 ± 92 | 1.83 ± 0.14 | 505.5 |
| 1 | H | CH₃ | (CH₂)₄ | Ph | 2 | 116 ± 7 | 281 ± 99 | 1.82 ± 0.08 | — |
| 5 | H | 2-Pr | (CH₂)₄ | Ph | 2 | 231 ± 35 | 705 ± 20 | 2.64 ± 0.27 | 49% @ 1 μM |
| 1 | H | H | (CH₂)₅ | Ph | 2 | 107 ± 59 | 348 ± 70 | 0.68 ± 0.23 | 46% @ 1 μM |
| 1 | H | H | E-CH₂CH=CH— | Ph | 2 | 133 ± 9 | 398 | 2.46 | 42.5 |
| 5 | H | H | (CH₂)₂ | CHPh₂ | 2 | 1483 ± 48 | 4007 ± 2257 | 4.52 | 36.6% @ 1 μM |
| 1 | H | H | (CH₂)₂ | OPh | 2 | 110 ± 14 | 534 ± 57 | 2.60 | 27.3% @ 1 μM |
| 7 | H | H | (CH₂)₂ | O-4-ClPh | 2 | 268 ± 38 | 5980 ± 3510 | 0.53 | 20 |
| 7 | H | H | (CH₂)₂ | O-3,4-Cl₂Ph | 2 | 400 ± 93 | 782 ± 13 | 0.65 | 376.67 |
| 7 | H | H | COCH₂ | O-3,4-Cl₂Ph | 2 | >10000 | >10000 | 64.5 | 48.9% @ 1 μM |
| 1 | H | H | (CH₂)₃ | OPh | 2 | 132 ± 16 | 262 ± 19 | 1.27 ± 0.26 | 24.7% @ 1 μM |
| 1 | H | H | (CH₂)₂ | O-4-F—Ph | 2 | 55 ± 9 | 148 ± 13 | 2.09 ± 77 | 22.9 |
| 1 | H | H | (CH₂)₃ | O-4-F—Ph | 2 | 88 ± 15 | 205 | 0.10 | 11.4 |
| 4 | F | H | (CH₂)₃ | OPh | 2 | 317 ± 49 | 1382 ± 188 | 37.3 ± 12.7 | 48 |
| 6 | H | H | (CH₂)₃ | OH | 2 | 836 ± 334 | 3332 ± 1808 | 12.3 ± 1.7 | 5.6 @ 1 μM |
| 7 | H | H | (CH₂)₂ | 2-phthalimido | 2 | 54 ± 19 | 76 ± 21 | 1.78 ± 0.63 | 4.9 @ 1 μM |
| 7 | H | H | (CH₂)₂ | 2-isoindolinyl | 2 | 8085 ± 1915 | >10000 | 52.1 | 72.2 @ 1 μM |
| 10 | H | H | (CH₂)₃ | 2-isoindolinyl | 2 | 141 ± 30 | 85 ± 26 | 2.2 ± 0.18 | 5.3 @ 1 μM |
| 9 | H | H | (CH₂)₃ | N(CH₃)COCH₂-3,4-Cl₂Ph | 2 | 1612 ± 660 | <10000 | 3.79 | 55.1 @ 1 μM |
| 9 | H | H | (CH₂)₂ | N(CH₃)CH₂CH₂-3,4-Cl₂Ph | 2 | 509 ± 63 | 474 ± 140 | 2.53 ± 0.16 | 18.4 @ 1 μM |
| 4 | F | H | (CH₂)₂ | 4-FPh | 2 | 129 ± 78 | 283 ± 71 | 0.28 ± 0.08 | 34.7 @ 1 μM |
| 4 | F | H | (CH₂)₃CO | 4-FPh | 2 | 55 | 408 | 0.22 | 0.82 |
| 4 | F | H | (CH₂)₃CO | 4-FPh | 2 | | | | 2.07 |
| 4 | F | H | (CH₂)₃ | 3-pyridyl | 2 | 44 ± 11 | 114 ± 10 | 12.2 ± 4.7 | 0% @ 1 μM |
| 1 | H | H | (CH₂)₄ | [spiro structure] | 2 | 50 | 836 | 2.38 ± 0.56 | 12% @ 1 μM |
| 1 (low Rf) | H | H | CH(CH₃)(CH₂)₂ | Ph | 2 | 119 | 1160 | 0.53 | 72.8% @ 1 μM |

TABLE 1-continued

In Vitro Sigma ([³H]DTG, [³H] (+)-3-PPP), Serotonin
5-HT₂ ([³H] ketanserin), and Dopamine D-2 ([³H] sulpiride) Binding

| | | | Formula I | | | Sigma IC$_{50}$, nM | | Dopamine D-2 Ki, μM | Serotonin 5-HT$_2$ Ki, nM |
|---|---|---|---|---|---|---|---|---|---|
| Example | X | R$_1$ | A | R$_2$ | n | [³H] DTG | [³H] (+)-3-PPP | sulpiride | ketanserin |
| 1 (high R$_f$) | H | H | CH(CH$_3$)(CH$_2$)$_2$ | Ph | 2 | 23 | 1500 | 1.11 | — |
| 2 | H | Ph | (CH$_2$)$_3$CO | 4-FPh | 2 | 528 | 510 | 0.84 | 813.8 |
| 1 | H | H | (CH$_2$)$_4$ | 4-FPh | 2 | 29 | 102 | 1.16 | 22.1 |
| 1 | H | H | (CH$_2$)$_4$CO | 4-FPh | 2 | 131 | 224 | 0.0035 | 1.5 |
| 1 | H | H | (CH$_2$)$_3$CO | Ph | 2 | — | — | — | — |
| 12 | F | H | — | H | 3 | 509 | 305 | 58.3 | 3000 |
| 12 | F | H | (CH$_2$)$_3$CO | 4-FPh | 3 | 23 | 103 | 0.2 | 2.5 |
| 12 | F | H | (CH$_2$)$_4$ | Ph | 3 | 42 | 117 | 1.87 | 172 |
| 12 | F | H | (CH$_2$)$_2$CH=C | (4-FPh)$_2$ | 3 | 1914 | 10000 | 3.73 | 625 |
| 11 | H | H | (CH$_2$)$_3$CO | 4-FPh | 3 | 43 | 89 | 0.038 | 0.46 |
| 11 | H | H | (CH$_2$)$_4$ | 4-FPh | 3 | 64 | 279 | 0.915 | 23.6 |
| 11 | H | H | (CH$_2$)$_2$CH=C | (4-FPh)$_2$ | 3 | 1883 | >10000 | 2.31 | >1000 |
| 11 | F | H | (CH$_2$)$_4$ | 4-FPh | 3 | 61 | 150 | 1.47 | 205 |

EXAMPLE 16

In Vivo Dopamine Antagonist Activity

To assess dopamine antagonist activity, the potency of compounds to inhibit apomorphine-induced climbing behavior was determined in mice. For these experiments, adult male CF-1 mice (Harlan Sprague-Dawley, Inc.) were housed in groups of 10 in standard rodent cages and allowed food and water ad libitum. Animals were used during the light phase of a 12 hour light/dark cycle with lights on at 6:00 a.m. and after at least 5 days of habituation. On the day of testing, mice were food deprived for 3–5 hours prior to oral (po) administration of vehicle or the compound of interest. Apomorphine (3 mg/kg) was administered (sc) 55 minutes later and mice were immediately placed into individual wire mesh cages (22×22×22 cm). Five minutes later, the amount of time mice spent with all four paws off the table top (climbing) was recorded for a maximum of 60 seconds by an observer blind to the treatment conditions. Similar recordings were also made at 10, 15 and 20 minutes post injection of apomorphine. For data analysis, the time spent climbing during each of the 4 observation periods was summed. The dose of compound expected to reduce climbing behavior to a level midway between that observed for vehicle and apomorphine control ($ED_{50}$) was calculated by least squares linear regression on the linear portion of the dose-effect curve after log 10 transformation of dose. Using this method, 11-[5-(4-fluorophenyl)-5-oxopentyl]-5,6,7,8,9,10-hexahydro-7,10-iminocyclohept[b]indole was found to inhibit dopamine receptors with a potency ($ED_{50}$) of 15.7 mg/kg following oral administration. For reference, the neuroleptic agent, haloperidol, exhibited a potency of 0.01 mg/kg following intraperitoneal (ip) administration.

EXAMPLE 17

In vivo Cataleptic Activity

The potency of selected compounds to produce catalepsy and motor impairment was evaluated according to the following methods. Groups of male CF-1 mice (Harlan Sprague-Dawley, Inc.), weighing 25–30 g, were food-deprived for 3–5 hours prior to oral administration of the compound of interest. These agents were suspended in 10% DMSO/10% Tween/80% distilled water vehicle and administered in a volume of 0.01 mL/g body weight. Fifty-five minutes after oral (po) administration, the presence or absence of catalepsy was determined by placing the forepaws on a rod (6 mm diameter) mounted 39 mm above the floor of the test chamber. Pressure was applied to immobilize the subject with its back in a concave position. Following removal of pressure, the latency to recover normal posture, as defined by the return of at least one forepaw to the floor of the chamber, or the placement of one hindlimb on the bar, was recorded. Mice were tested three times and considered cataleptic if recovery was not apparent within 30 seconds during any of the three trials. Following determination of catalepsy and at 60 minutes post administration of compound, motor impairment was determined by placing mice on a rotating knurled bar (Rotorod, Ugo Basile model 7600; 6–7 revolutions per minute; 3.8 cm diameter). Mice were tested up to three times; mice failing to remain on the bar for 60 sec during all three tests were considered impaired.

Results reported in Table 2 indicate that catalepsy was not observed in mice at any dose of 11-[5-(4-fluorophenyl)-5-oxopentyl]-5,6,7,8,9,10-hexahydro-7,10-iminocyclohept[b]indole or 2-fluoro-11-[4-(4fluorophenyl)-4-oxo-butzl]-5,6,7,8,9,10-hexahydro-7,10-iminocyclohept [b]indole tested. Impairment of rotorod performance was noted at 300–500 mg/kg whereas compound potency to block dopamine receptors (apomorphine climbing test) was determined to be 15.7 mg/kg.

TABLE 2

| Compound | Dose (mg/kg) | n | Cataleptic Number | Failing Rotorod Number |
|---|---|---|---|---|
| 11-[5-(4-fluorophenyl)-5-oxopentyl]-5,6,7,-8,9,10-hexahydro-7, 10-iminocyclohept[b]indole | 178 | 4 | 0 | 0 |
|  | 300 | 4 | 0 | 1 |
|  | 500 | 4 | 0 | 4 |
| 2-fluoro-11-[4-(4-fluorophenyl)-4-oxo-butyl]-5,6,7,8,9,10-hexahydro-7,10-iminocyclohept[b]indole | 178 | 4 | 0 | 0 |
|  | 300 | 4 | 0 | 2 |
|  | 500 | 3 | 0 | 1 |

EXAMPLE 18

| Ingredients |
|---|
| 11-[4-(4-fluorophenyl)-4-oxobutyl]-5,6,7,8,9,10-hexahydro-7,10-iminocyclohept[b]indole |
| Magnesium Stearate |
| Lactose |

The above ingredients are mixed, passed through a No. 40 mesh screen, remixed and filled into No. 2 capsules.

| Ingredients | mg per Tablet |
|---|---|
| 11-(4-phenyl-2-butyl)-5,6,7,8,9,10-hexahydro-7,10-iminocyclohept[b]indole (low $R_f$) | 10 |
| Calcium Sulfate, dihydrate | 200 |
| Sucrose | 25 |
| Talc | 5 |
| Stearic acid | 3 |

Sucrose, calcium sulfate and the 7,10-iminocyclohept[b]indole are thoroughly mixed and granulated with hot 10% gelatin solution. The wetted mass is passed through a No. 6 standard mesh screen onto drying trays. The granules are dried at 120° F. and passed through a No. 20 mesh screen. These granules are then mixed with starch, talc and stearic acid, passed through a No. 60 mesh screen and then compressed into tablets.

What is claimed is:

1. A chemical compound of the formula:

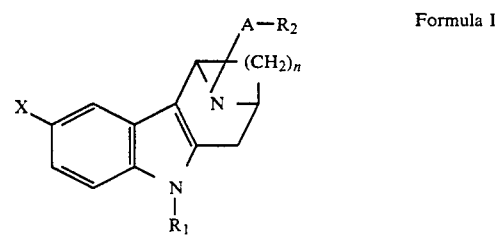

Formula I in which:

X represents hydrogen, fluoro, chloro, or bromo;

$R_1$ represents hydrogen, $C_{1-4}$ alkyl, benzyl, substituted benzyl, substituted phenyl or, provided X is not hydrogen, phenyl wherein said substitutions are selected from the group consisting of halogen, hydroxy, $C_{1-4}$ alkoxy, $C_{1-4}$ alkyl or any combination thereof;

A represents $C_{1-6}$ alkylene, or $C_{1-6}$ alkylene wherein one of the methylene carbons is replaced by a carbonyl group;

$R_2$ represents phenyl, substituted phenyl, benzyl, substituted benzyl, phenoxy, substituted phenoxy, diphenyl $C_{1-4}$ alkyl, pyridyl, 2-isoindolinyl, 2-(1,3-dioxoindolinyl), 8-(7,9-dioxo-8-azaspiro[4.5]decanyl), N-(3,4-dichlorophenethyl)-N-methylamino, N-(3,4-dichlorophenylacetyl)-N-methylamino, hydroxyl or $C_{1-4}$ alkoxy wherein said substitutions are selected from the group consisting of halogen, hydroxy, $C_{1-4}$ alkoxy, $C_{1-4}$ alkyl or any combination thereof; and n=2 or 3 or a pharmaceutically acceptable acid addition salt thereof.

2. A compound of claim 1 wherein X is hydrogen or fluoro.

3. A compound of claim 1 wherein $R_1$ is hydrogen.

4. A compound of claim 1 wherein $R_2$ is phenyl, 4-fluorophenyl, phenoxy, 4-fluorophenoxy, 2-isoindolinyl, or 8-(7,9-dioxo-8-azaspiro[4.5]decanyl).

5. A compound of claim 1 that is:
11-(4-phenybutyl)-5,6,7,8,9,10-hexahydro-7,10-iminocyclohept[b]indole;
11-(5-phenylpentyl)-5,6,7,8,9,10-hexahydro-7,10-iminocyclohept[b]indole;
11-[4-(4-fluorophenyl)-4-oxobutyl]-5,6,7,8,9,10-hexahydro-7,10-iminocyclohept-[b]indole; or
11-[4-(4-fluorophenyl)-4-oxobutyl]-5-phenyl-5,6,7,8,9,10-hexahydro-7,10-iminocyclohept[b]indole.

6. A compound of claim 1 that is
11-benzyl-5,6,7,8,9,10-hexahydro-7,10-iminocyclohept-[b]indole; 11-benzyl-2-fluoro-5,6,7,8,9,10-hexahydro-7,10iminocyclohept[b]indole;
11-(3-phenylpropyl)-5,6,7,8,9,10-hexahydro-7,10-iminocyclohept[b]indole;
2-fluoro-11-(4-phenylbutyl)-5,6,7,8,9,10-hexahydro-7,10-iminocyclohept[b]indole;
11-(4-phenyl-2-butyl)-5,6,7,8,9,10-hexahydro-7,10-iminocyclohept[b]indole;
11-(4-phenoxybutyl)-5,6,7,8,9,10-hexahydro-7,10-iminocyclohept[b]indole;
11-(3-phenoxypropyl)-5,6,7,8,9,10-hexahydro-7,10-iminocyclohept[b]indole;
11-[3-(4-fluorophenoxy)propyl]-5,6,7,8,9,10-hexahydro-7,10-iminocyclohept[b]indole;
11-[2-(2-isoindolinyl)ethyl]-5,6,7,8,9,10-hexahydro-7,10-iminocyclohept[b]indole;
2-fluoro-11-[3-(2-isoindolinyl)propyl]-5,6,7,8,9,10-hexahydro-7,10-iminocyclohept[b]indole;
2-fluoro-11-[4-(4-fluorophenyl)-4-oxobutyl]-5,6,7,8,9,10-hexahydro-7,10-iminocyclohept[b]indole
11-{8-(7,9-dioxo-8-azaspiro[4.5]decanyl)}-5,6,7,8,9,10-hexahydro-7,10-iminocyclohept[b]indole;
11-[4-(4-fluorophenyl)butyl]-5,6,7,8,9,10-hexahydro-7,10-iminocyclohept[b]indole;
11-[5-(4-fluorophenyl)-5-oxopentyl]-5,6,7,8,9,10-hexahydro-7,10-iminocyclohept[b]indole;
11-(4-phenyl-4-oxobutyl)-5,6,7,8,9,10-hexahydro-7,10-iminocyclohept[b]indole;
2-fluoro-12-[4-(4-fluorophenyl)-4-oxobutyl]-6,7,8,9,10,11-hexahydro-7,11-imino-5H-cyclooct[b]indole;
2-fluoro-12-(4-phenylbutyl)-6,7,8,9,10,11-hexahydro-7,11-imino-5H-cyclooct[b]indole;
12-[4-(4-fluorophenyl)-4-oxo-butyl]-6,7,8,9,10,11-hexahydro-7,11-imino-5H-cyclooct[b]indole;
12-[4-(4-fluorophenyl)butyl]-6,7,8,9,10,11-hexahydro-7,11-imino-5H-cyclooct[b]indole; or
2-fluoro-12-[4-(4-fluorophenyl)butyl]-6,7,8,9,10,11-hexahydro-7,11-imino-5H-cyclooct[b]indole.

7. A pharmaceutical composition useful in treatment of psychoses comprising a pharmaceutically acceptable carrier and a compound of the following formula:

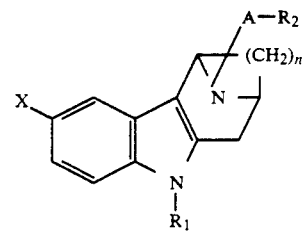

Formula II in which:

X represents hydrogen, fluoro, chloro, or bromo;

$R_1$ represents hydrogen, $C_{1-4}$ alkyl, benzyl, substituted benzyl, phenyl or substituted phenyl wherein said substitutions are selected from the group consisting of halogen, hydroxy, $C_{1-4}$ alkoxy, $C_{1-4}$ alkyl or any combination thereof;

A represents $C_{1-6}$ alkylene, or $C_{1-6}$ alkylene wherein one of the methylene carbons is replaced by a carbonyl group;

$R_2$ represents phenyl, substituted phenyl, benzyl, substituted benzyl, phenoxy, substituted phenoxy, diphenyl $C_{1-4}$ alkyl, pyridyl, 2-isoindolinyl, 2-(1,3-dioxoindolinyl), 8-(7,9-dioxo-8-azaspiro[4.5]decanyl), N-(3,4-dichlorophenethyl)-N-methylamino, N-(3,4-dichlorophenylacetyl)-N-methylamino, hydroxyl or $C_{1-4}$ alkoxy wherein said substitutions are selected from the group consisting of halogen, hydroxy, $C_{1-4}$ alkoxy, $C_{1-4}$ alkyl or any combination thereof; and n=2 or 3 or a pharmaceutically acceptable acid addition salt thereof.

8. A pharmaceutical composition of claim 7 wherein the compound is
11-(4-phenylbutyl)-5,6,7,8,9,10-hexahydro-7,10-iminocyclohept[b]indole;
11-(5-phenylpentyl)-5,6,7,8,9,10-hexahydro-7,10-iminocyclohept[b]indole;
11-[4-(4-fluorophenyl)-4-oxobutyl]-5,6,7,8,9,10-hexahydro-7,10-iminocyclohept-[b]indole; or
11-[4-(4-fluorophenyl)-4-oxobutyl]-5-phenyl-5,6,7,8,9,10-hexahydro-7,10-iminocyclohept[b]indole.

9. A pharmaceutical composition of claim 7 wherein the compound is
11-benzyl-5,6,7,8,9,10-hexahydro-7,10-iminocyclohept[b]indole;

11-benzyl-2-fluoro-5,6,7,8,9,10-hexahydro-7,10-iminocyclohept[b]indole;

11-(3-phenylpropyl)-5,6,7,8,9,10-hexahydro-7,10-iminocyclohept[b]indole;

2-fluoro-11-(4-phenylbutyl)-5,6,7,8,9,10-hexahydro-7,10-iminocyclohept[b]indole;

11-(4-phenyl-2-butyl)-5,6,7,8,9,10-hexahydro-7,10-iminocyclohept[b]indole;

11-(4-phenoxybutyl)-5,6,7,8,9,10-hexahydro-7,10-iminocyclohept[b]indole;

11-(3-phenoxypropyl)-5,6,7,8,9,10-hexahydro-7,10-iminocyclohept[b]indole;

11-[3-(4-fluorophenoxy)propyl]-5,6,7,8,9,10-hexahydro-7,10-iminocyclohept[b]indole;

11-[2-(2-isoindolinyl)ethyl]-5,6,7,8,9,10-hexahydro-7,10-iminocyclohept[b]indole;

2-fluoro-11-[3-(2-isoindolinyl)propyl]-5,6,7,8,9,10-hexahydro-7,10-iminocyclohept[b]indole;

2-fluoro-11-[4-(fluorophenyl)-4-oxobutyl]-5,6,7,8,9,10-hexahydro-7,10-iminocyclohept[b]indole;

11-{8-(7,9-dioxo-8-azaspiro[4.5]decanyl)}-5,6,7,8,9,10-hexahydro-7,10-iminocyclohept[b]indole;

11-[4-(4-fluorophenyl)butyl]-5,6,7,8,9,10-hexahydro-7,10-iminocyclohept[b]indole;

11-[5-(4-fluorophenyl)-5-oxopentyl]-5,6,7,8,9,10-hexahydro-7,10-iminocyclohept[b]indole;

11-(4-phenyl-4-oxobutyl)-5,6,7,8,9,10-hexahydro-7,10-iminocyclohept[b]indole;

2-fluoro-12-[4-(4-fluorophenyl)-4-oxobutyl]-6,7,8,9,10,11-hexahydro-7,11-imino-5H-cyclooct[b]indole;

2-fluoro-12-(4-phenylbutyl)-6,7,8,9,10,11-hexahydro-7,11-imino-5H-cyclooct[b]indole;

12-[4-(4-fluorophenyl)-4-oxo-butyl]-6,7,8,9,10,11-hexahydro-7,11-imino-5H-cyclooct[b]indole;

12-[4-(4-fluorophenyl)butyl]-6,7,8,9,10,11-hexahydro-7,11-imino-5H-cyclooct[b]indole; or 2-fluoro-12-[4-(4-fluorophenyl)butyl]-6,7,8,9,10,11-hexahydro-7,11-imino-5H-cyclooct[b]indole.

10. A method for treating sigma, dopamine, or serotonin receptor-related psychoses which comprises administering to a subject in need thereof an effective amount of a compound of the following Formula II:

$$\text{Formula II}$$

in which:

X represents hydrogen, fluoro, chloro, or bromo;

$R_1$ represents hydrogen, $C_{1-4}$ alkyl, benzyl, substituted benzyl, phenyl or substituted phenyl wherein said substitutions are selected from the group consisting of halogen, hydroxy, $C_{1-4}$ alkoxy, $C_{1-4}$ alkyl or any combination thereof;

A represents $C_{1-6}$ alkylene, or $C_{1-6}$ alkylene wherein one of the methylene carbons is replaced by a carbonyl group;

$R_2$ represents phenyl, substituted phenyl, benzyl, substituted benzyl, phenoxy, substituted phenoxy, diphenyl $C_{1-4}$ alkyl, pyridyl, 2-isoindolinyl, 2-(1,3-dioxoindolinyl), 8-(7,9-dioxo-8-azaspiro[4.5]decanyl), N-(3,4-dichlorophenethyl)-N-methylamino, N-(3,4-dichlorophenylacetyl)-N-methylamino, hydroxyl or $C_{1-4}$ alkoxy wherein said substitutions are selected from the group consisting of halogen, hydroxy, $C_{1-4}$ alkoxy, $C_{1-4}$ alkyl or any combination thereof; and n=2 or 3 or a pharmaceutically acceptable acid addition salt thereof.

11. A method of claim 10 wherein the compound is 11-(4-phenylbutyl)-5,6,7,8,9,10-hexahydro-7,10-iminocyclohept[b]indole;

11-(5-phenylpentyl)-5,6,7,8,9,10-hexahydro-7,10-iminocyclohept[b]indole;

11-[4-(4-fluorophenyl)-4-oxobutyl]-5,6,7,8,9,10-hexahydro-7,10-iminocyclohept[b]indole; or 11-[4-(4-fluorophenyl)-4-oxobutyl]-5-phenyl-5,6,7,8,9,10-hexahydro-7,10-iminocyclohept[b]indole.

12. A method of claim 10 wherein the compound is 11-benzyl-5,6,7,8,9,10-hexahydro-7,10-iminocyclohept[b]indole;

11-benzyl-2-fluoro-5,6,7,8,9,10-hexahydro-7,10-iminocyclohept[b]indole;

11-(3-phenylpropyl)-5,6,7,8,9,10-hexahydro-7,10-iminocyclohept[b]indole;

2-fluoro-11-(4-phenylbutyl)-5,6,7,8,9,10-hexahydro-7,10-iminocyclohept[b]indole;

11-(4-phenyl-2-butyl)-5,6,7,8,9,10-hexahydro-7,10-iminocyclohept[b]indole;

11-(4-phenoxybutyl)-5,6,7,8,9,10-hexahydro-7,10-iminocyclohep[b]indole;

11-(3-phenoxypropyl)-5,6,7,8,9,10-hexahydro-7,10-iminocyclohept-[b]indole;

11-[3-(4-fluorophenoxy)propyl]-5,6,7,8,9,10-hexahydro-7,10-iminocyclohept[b]indole;

11-[2-(2-isoindolinyl)ethyl]-5,6,7,8,9,10-hexahydro-7,10-iminocyclohept[b]indole;

2-fluoro-11-[3-(2-isoindolinyl)propyl]-5,6,7,8,9,10-hexahydro-7,10-iminocyclohept[b]indole;

2-fluoro-11-[4-(4-fluorophenyl)-4-oxobutyl]-5,6,7,8,9,10-hexahydro-7,10-iminocyclohept[b]indole;

11-{8-(7,9-dioxo-8-azaspiro[4.5]decanyl)}-5,6,7,8,9,10-hexahydro-7,10-iminocyclohept[b]indole;

11-[4-(4-fluorophenyl)butyl]-5,6,7,8,9,10-hexahydro-7,10-iminocyclohept[b]indole;

11-[5-(4-fluorophenyl)-5-oxopentyl]-5,6,7,8,9,10-hexahydro-7,10-iminocyclohept[b]indole;

11-(4-phenyl-4-oxobutyl)-5,6,7,8,9,10-hexahydro-7,10-iminocyclohept[b]indole;

2-fluoro-12-[4-(4-fluorophenyl)-4-oxobutyl]-6,7,8,9,10,11-hexahydro-7,11-imino-5H-cyclooct[b]indole;

2-fluoro-12-(4-phenylbutyl)-6,7,8,9,10,11-hexahydro-7,11-imino-5H-cyclooct[b]indole;

12-[4-(4-fluorophenyl)-4-oxobutyl]-6,7,8,9,10,11-hexahydro-7,11-imino-5H-cyclooct[b]indole;

12-[4-(4-fluorophenyl)butyl]-6,7,8,9,10,11-hexahydro-7,11-imino-5H-cyclooct[b]indole; or 2-fluoro-12-[4-(4-fluorophenyl)butyl]-6,7,8,9,10,11-hexahydro-7,11-imino-5H-cyclooct[b]indole.

13. A method for blocking 5-HT$_2$ receptors that comprises administering to a subject in need thereof an effective amount of a compound of the following formula:

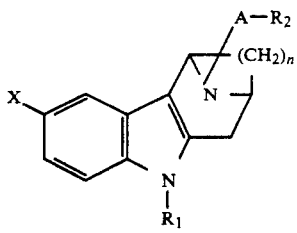
Formula II in which:

X represents hydrogen, fluoro, chloro, or bromo;

$R_1$ represents hydrogen, $C_{1-4}$ alkyl, benzyl, substituted benzyl, phenyl or substituted phenyl wherein said substitutions are selected from the group consisting of halogen, hydroxy, $C_{1-4}$ alkoxy, $C_{1-4}$ alkyl or any combination thereof;

A represents $C_{1-6}$ alkylene, or $C_{1-6}$ alkylene wherein one of the methylene carbons is replaced by a carbonyl group;

$R_2$ represents phenyl, substituted phenyl, benzyl, substituted benzyl, phenoxy, substituted phenoxy, diphenyl $C_{1-4}$ alkyl, pyridyl, 2-isoindolinyl, 2-(1,3-dioxoindolinyl), 8-(7,9-dioxo-8-azaspiro[4.5]decanyl), N-(3,4-dichlorophenethyl)-N-methylamino, N-(3,4-dichlorophenylacetyl)-N-methylamino, hydroxyl or $C_{1-4}$ alkoxy wherein said substitutions are selected from the group consisting of halogen, hydroxy, $C_{1-4}$ alkoxy, $C_{1-4}$ alkyl or any combination thereof; and n=2 or 3 or a pharmaceutically acceptable acid addition salt thereof.

14. A method of claim 13 wherein the compound is
11-(4-phenylbutyl)-5,6,7,8,9,10-hexahydro-7,10-iminocyclohept[b]indole;
11-(5-phenylpentyl)-5,6,7,8,9,10-hexahydro-7,10-iminocyclohept[b]indole;
11-[4-(4-fluorophenyl)-4-oxobutyl]-5,6,7,8,9,10-hexahydro-7,10-iminocyclohept[b]indole; or
11-[4-(4-fluorophenyl)-4-oxobutyl]-5-phenyl-5,6,7,8,9,10-hexahydro-7,10-iminocyclohept[b]indole.

15. A method of claim 13 wherein the compound is
11-benzyl-5,6,7,8,9,10-hexahydro-7,10-iminocyclohept[b]indole; 11-benzyl-2-fluoro-5,6,7,8,9,10-hexahydro-7,10-iminocyclohept[b]indole;
11-(3-phenylpropyl)-5,6,7,8,9,10-hexahydro-7,10-iminocyclohept[b]indole;
2-fluoro-11-(4-phenylbutyl)-5,6,7,8,9,10-hexahydro-7,10-iminocyclohept[b]indole;
11-(4-phenyl-2-butyl)-5,6,7,8,9,10-hexahydro-7,10-iminocyclohept[b]indole;
11-(4-phenoxybutyl)-5,6,7,8,9,10-hexahydro-7,10-iminocyclohept[b]indole;
11-(3-phenoxypropyl)-5,6,7,8,9,10-hexahydro-7,10-iminocyclohept-[b]indole;
11-[3-(4-fluorophenoxy)propyl]-5,6,7,8,9,10-hexahydro-7,10-iminocyclohept[b]indole;
11-[2-(2-isoindolinyl)ethyl]-5,6,7,8,9,10-hexahydro-7,10-iminocyclohept[b]indole;
2-fluoro-11-[3-(2-isoindolinyl)propyl]-5,6,7,8,9,10-hexahydro-7,10-iminocyclohept[b]indole;
2-fluoro-11-[(4-fluorophenyl)-4-oxobutyl]-5,6,7,8,9,10-hexahydro-7,10-iminocyclohept[b]indole;
11-{8-(7,9-dioxo-8-azaspiro[4.5]decanyl)}-5,6,7,8,9,10-hexahydro-7,10-iminocyclohept[b]indole;
11-[4-(4-fluorophenyl)butyl]-5,6,7,8,9,10-hexahydro-7,10-iminocyclohept[b]indole;
11-[5-(4-fluorophenyl)-5-oxopentyl]-5,6,7,8,9,10-hexahydro-7,10-iminocyclohept[b]indole;
11-(4-phenyl-4-oxobutyl)-5,6,7,8,9,10-hexahydro-7,10-iminocyclohept[b]indole;
2-fluoro-12-[4-(4-fluorophenyl)-4-oxobutyl]-6,7,8,9,10,11-hexahydro-7,11-imino-5H-cyclooct[b]indole;
2-fluoro-12-(4-phenylbutyl)-6,7,8,9,10,11-hexahydro-7,11-imino-5H-cyclooct[b]indole;
12-[4-(4-fluorophenyl)-4-oxo-butyl]-6,7,8,9,10,11-hexahydro-7,11-imino-5H-cyclooct[b]indole;
12-[4-(4-fluorophenyl)butyl]-6,7,8,9,10,11-hexahydro-7,11-imino-5H-cyclooct[b]indole; or
2-fluoro-12-[4-(4-fluorophenyl)butyl]-6,7,8,9,10,11-hexahydro-7,11-imino-5H-cyclooct[b]indole.

* * * * *

UNITED STATES PATENT AND TRADEMARK OFFICE
CERTIFICATE OF CORRECTION

PATENT NO. : 5,250,537
DATED : 10/5/93
INVENTOR(S) : Richard E. Mewshaw et al

It is certified that error appears in the above-indentified patent and that said Letters Patent is hereby corrected as shown below:

On the title page, item [54] and in column 1, lines 2-5, the title should read as follows:

--5, 6, 7, 8, 9, 10-HEXAHYDRO-7, 10-IMINOCYCLOHEPT[B]INDOLE -6, 7, 8, 9, 10, 11-HEXAYDRO-7, 11-IMINO-5H-CYCLOOCT[B]INDOLE AND SUBSTITUTED DERIVATIVES--.

Column 23, line 31, replace "11-(4-phenybutyl)" with --11-(4-phenylbutyl)--;
line 44, replace "hexahydro-7, 10iminocyclohept[b]indole" with --hexahydro-7, 10-iminocyclohept[b]indole--.

Column 26, line 34, replace "iminocyclohep[b]indole" with --iminocyclohept-[b]indole; and lines 56-57, replace "6, 7, 8, 9, 10, 11-hexahydro-7, 11-imin -H-cycloact[b]indole" with --6, 7, 8, 9, 10, 11-hexahydro-7, 11-imino-5H-cyclooct[b]indole--.

Signed and Sealed this

Twelfth Day of September, 1995

Attest:

BRUCE LEHMAN

Attesting Officer    Commissioner of Patents and Trademarks